United States Patent
Orr, III

(10) Patent No.: US 6,369,289 B1
(45) Date of Patent: Apr. 9, 2002

(54) METHOD AND MANUFACTURE OF A WOUND DRESSING FOR COVERING AN OPEN WOUND

(75) Inventor: Robert H. Orr, III, Attleboro, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 09/611,482

(22) Filed: Jul. 7, 2000

(51) Int. Cl.[7] ................................................ A61F 13/00
(52) U.S. Cl. ............................ 602/48; 602/41; 602/42; 604/304
(58) Field of Search ...................... 602/41–59; 128/888, 128/889; 424/78.08, 78.26, 78.34, 78.35, 404–407, 409, 411

(56) References Cited

U.S. PATENT DOCUMENTS

| | | |
|---|---|---|
| 2,336,605 A | 12/1943 | Ernsberger et al. |
| 2,863,919 A | 12/1958 | Birtwell et al. |
| 2,990,425 A | 6/1961 | Senior |
| 3,860,729 A | 1/1975 | Strandskov et al. |
| 4,014,676 A | 3/1977 | Carter et al. |
| 4,022,836 A | 5/1977 | Hammen et al. |
| 4,032,292 A | 6/1977 | Jones |
| 4,405,645 A | 9/1983 | Rothlisberger et al. |
| 4,478,821 A | 10/1984 | Carrillo |
| 4,587,266 A | 5/1986 | Verdicchio |
| 4,643,180 A | 2/1987 | Feld et al. |
| 4,643,181 A | 2/1987 | Brown |
| 4,655,756 A | 4/1987 | Fawkes |
| 4,678,704 A | 7/1987 | Fellows |
| 4,728,323 A | 3/1988 | Matson |
| 4,758,595 A | 7/1988 | Ogunbiyi et al. |
| 4,837,079 A | 6/1989 | Quantrille et al. |
| 4,838,253 A | 6/1989 | Brassington et al. |
| 4,842,597 A | 6/1989 | Brook |
| 5,019,096 A | 5/1991 | Fox, Jr. et al. |
| 5,098,417 A | 3/1992 | Yamazaki et al. |
| 5,141,803 A | 8/1992 | Pregozen |
| 5,527,271 A | 6/1996 | Shah et al. |
| 5,700,742 A | 12/1997 | Payne |
| 5,817,325 A * | 10/1998 | Sawan et al. ................ 424/411 |
| 5,856,248 A | 1/1999 | Weinberg |
| 5,993,840 A | 11/1999 | Fawkes et al. |

FOREIGN PATENT DOCUMENTS

| | | |
|---|---|---|
| CA | 1223208 | 6/1987 |
| GB | 2300200 | 10/1996 |
| WO | 98/18330 | 5/1998 |

\* cited by examiner

Primary Examiner—Kim M. Lewis

(57) ABSTRACT

A method for covering an open wound by contacting the wound with a cellulosic bandage having a calculated amount of PHMB applied to the bandage. The cellulosic bandage can be prepared by providing at least one rolled beam of cellulosic material onto a perforated drum, inserting the beam of material into an enclosed vessel, adding PHMB into the vessel, and circulating the PHMB for a predetermined period of time.

26 Claims, 1 Drawing Sheet

METHOD AND MANUFACTURE OF A WOUND DRESSING FOR COVERING AN OPEN WOUND

BACKGROUND OF THE INVENTION

A. Field of the Invention

The present invention relates to a method for covering an open wound. The present invention further relates to a method of preparing a cellulosic wound dressing which is antimicrobially treated and the resulting bandage.

B. Description of the Related Art

Wound dressings have been used in the medical industry for years to help heal and protect open wounds. Cellulosic bandages used in the medical industry are typically made from woven greige cloth, which is cloth that is unbleached and unfinished. The cloth is bleached to whiten the fabric, and is converted into a gauze bandage.

Ideally, cellulosic wound dressings should have certain properties to aid in proper healing of the wound. For instance, U.S. Pat. No. 5,527,271 to Shah et al. discloses a thermoplastic hydrogel impregnated composite material for wound dressings. The hydrogel is applied to the cotton gauze wound dressing to prevent the wound dressing from adhering to the wound during the healing process.

Similarly, U.S. Pat. No. 4,838,253 to Brassington et al. discloses a silicone gel coated permeable wound dressing which is prepared by coating a sheet of apertured material with a non-crosslinked silicone material and then causing it to crosslink. The disclosed wound dressings have increased absorbency as well as having properties which prevent wound dressings from adhering to the wound surface.

More importantly, however, a wound dressing should have antimicrobial properties which kill airborne bacteria upon contact with the dressing, to prevent bacteria from entering the wound and migrating through the wound dressing. Accordingly, there have been many efforts in the past to process a cellulosic wound dressing that has antimicrobial properties.

For instance, U.S. Pat. No. 4,728,323 to Matson discloses an antimicrobial wound dressing comprised of a substrate coated with an antimicrobially effective film of a silver salt. The antimicrobial wound dressing is prepared by depositing certain silver salts onto a wound dressing surface. However, the process for treating the wound dressing is rather time consuming and complex, as the antimicrobial treatment must be applied by a separate apparatus, namely a sputter coating apparatus.

EP 0 136 900 and Canadian Pat. No. 1,223,208 disclose a nonwoven fabric which possesses antimicrobial properties and is useful in the manufacture of surgical drapes. The nonwoven fabric is treated with an antimicrobial agent which has activity against a broad spectrum of Gram negative and Gram positive bacteria and which will not become inactivated by blood serum. The antimicrobial agent used is polyhexamethylene biguanide (hereinafter "PHMB"). As noted in the background section, PHMB has been suggested as having antimicrobial utility in the treatment of textile materials. U.S. Pat. Nos. 2,336,605; 2,990,425; 4,022,836; 2,863,919 disclose this utility.

In addition, PHMB has been used in water treatment for controlling the growth of algae as disclosed in U.S. Pat. No. 4,014,676 to Carter et al., for the treatment of dandruff as disclosed in U.S. Pat. No. 4,405,645 to Röthlisberger et al., and as a contact lens preservative as disclosed in U.S. Pat. No. 4,758,595 to Ogunbiyi et al.

More recently, PHMB has been used in woven textile materials, such as clothing. For instance, GB 2 300 200 discloses a cellulosic substrate which is treated with a polymeric biguanide followed by an antibonding agent to confer antimicrobial properties to the cellulosic substrate. The treated substrate has an ancillary characteristic of reducing the propensity of the substrate to yellow on contact. Treated articles may be formed as shirts, underwear, uniforms, and socks, and is particularly useful for articles that become soiled and susceptible to microbial growth. It is important to note that the use of the antibonding agent helps prevent the normal reaction of PHMB to humans, had the PHMB been used alone. PHMB, if used alone to treat the article, could cause various skin disorders, such as redness, tenderness, and hives.

WO 98/18330 discloses non-leaching antimicrobial materials capable of killing microorganisms on contact, but which do not leach significant amounts of antimicrobial materials into the surrounding environment. The antimicrobial material comprises a complex of a polycationic ligand compound and a metallic material, where the polycationic compound is a polymer. In a preferred embodiment, the polymeric material is PHMB, the crosslinking agent is non-methylene bisdiglycidylaniline (hereinafter "MBDGA"), and the metallic material is a silver salt, wherein the silver salt is transferred from the coating to the microorganism and accumulates to toxic levels to kill the microorganism. The disclosed antimicrobial compositions can be used on various types of substrates, such as woods, metals, paper, clothing, glasses, and ceramics. In addition, the antimicrobial materials in powder form can be dispersed or dissolved in a carrier and used as a topical antiseptic, a topical dressing for a wound or a topical disinfectant. However, the disclosed composition can only be added to substrates as a surface coating. Therefore, the disclosed composition, if applied as a surface coating, would not protect migration of the bacteria throughout the wound dressing.

U.S. Pat. No. 5,019,096 to Fox, Jr. et al. discloses an infection-resistant composition for medical devices and surfaces and methods for preparing and using same. The method includes incorporating an effective amount of antimicrobial agent in a matrix comprising a polymeric component, wherein the matrix is effective to provide controlled release of the antimicrobial agent at a level sufficient to suppress infection when in contact with fluids. The antimicrobial agent is disclosed as including synergistically effective amounts of a silver salt and a biguanide. Preferably, the final coating contains from 10 to 70% by weight of the microbial agent. This composition is meant only as a coating and would not prevent microbial migration through a wound dressing.

BRIEF SUMMARY OF THE INVENTION

In one aspect, the present invention provides a method of covering and protecting an open wound from microbial contamination, by dressing the wound with a cellulosic wound dressing having an antimicrobial amount of PHMB applied to the bandage.

In a further important aspect, the present invention provides a method of covering an open wound by directly contacting the wound with a cellulosic wound dressing having an antimicrobial amount of PHMB applied to the bandage, without having an intermediate layer between the antimicrobially treated bandage and the open wound.

In yet a further aspect, the present invention provides a wound dressing consisting essentially of PHMB.

In a further aspect, the present invention provides a method of manufacturing a wound dressing having antimicrobial properties. The method comprises:

A) providing at least one rolled beam of cellulosic material;

B) inserting the beam of material into an enclosed vessel;

C) adding PHMB into the vessel; and

D) circulating the PHMB for a predetermined period of time.

In a still further aspect, the present invention provides a wound dressing manufactured according to the claimed method.

BRIEF DESCRIPTION OF THE DRAWINGS

Further features and characteristics of the present invention will become more apparent from the following detailed description considered in reference to the accompanying drawing FIGURE which is a schematic of the manufacturing process according to the present invention.

DETAILED DESCRIPTION OF THE INVENTION

Figure 1:
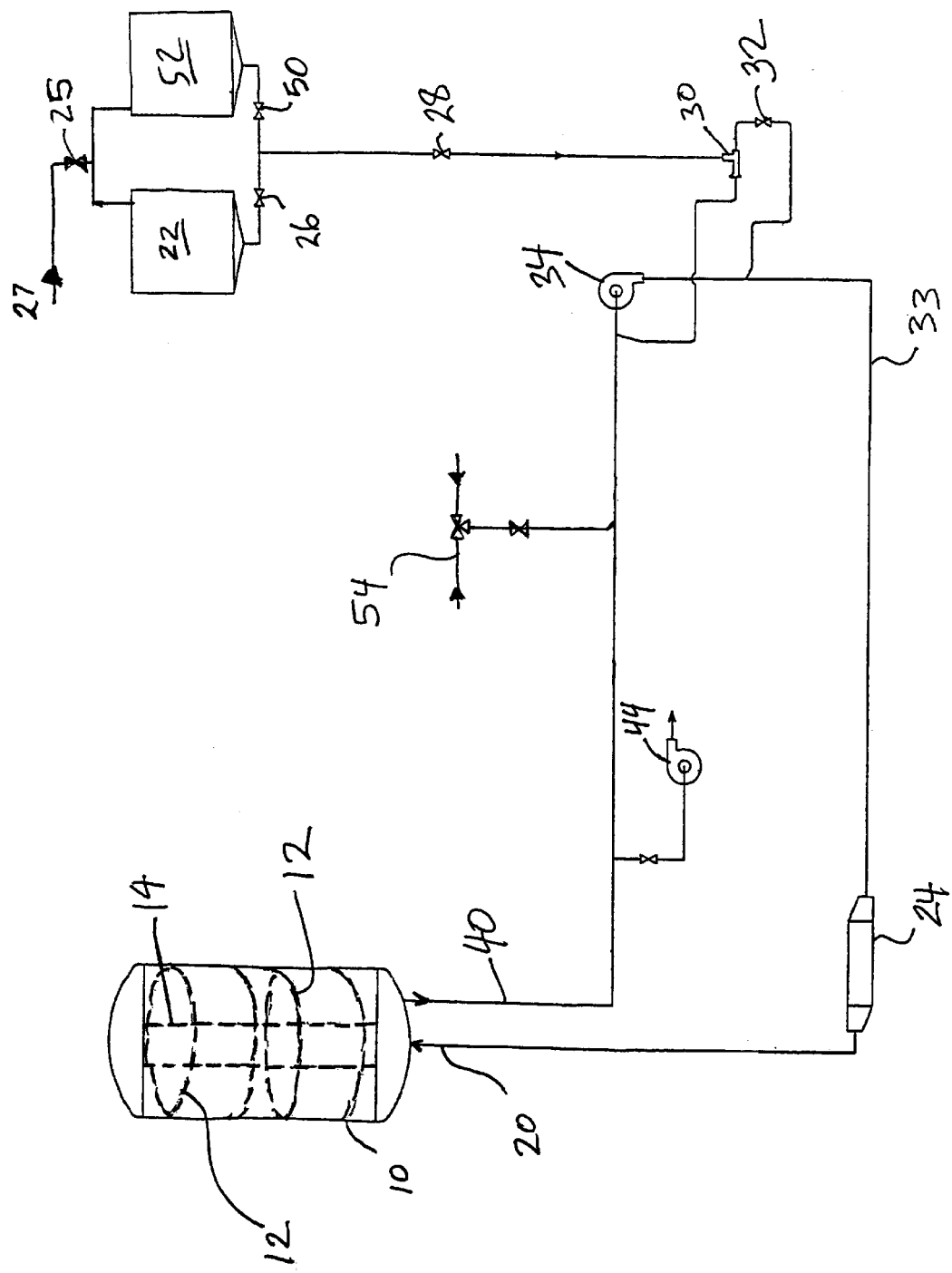

As noted above, one aspect of the present invention relates to a method of covering a wound with a cellulosic bandage having a calculated amount of PHMB applied to the bandage. PHMB is known for its antimicrobial properties, but has not been used as a component to prevent bacterial infection of a wound. Primarily, this is so because PHMB, when used alone and not in combination with another substance, has the tendency to irritate the skin of human beings, and has even stronger effects on the delicate nature of an open wound.

The present invention discovers that PHMB can be used alone on cellulosic fabric for covering a wound without causing irritation of the skin or wound, yet providing a wound dressing with sufficiently strong antimicrobial properties. The cellulosic wound dressing according to the present invention consists essentially of an antimicrobial amount of PHMB. The term "consisting essentially of" is meant to exclude additional components such as an antibonding agent which have been used in the past to prevent the normal reaction of PHMB to humans. In addition, PHMB functions as the primary antimicrobial agent, yet without requiring an intermediate layer between the antimicrobially treated bandage and the open wound.

In particular, the antimicrobial amount of PHMB applied to the material is preferably between 500–3000 ppm, and most preferably between 1500–2500 ppm, as determined by extraction. However, this amount may be lower because efficacy is still attained at levels lower than 500 ppm. The antimicrobial amount is defined as the amount of PHMB applied to the wound dressing that is needed for providing sufficient antimicrobial characteristics yet without causing irritation of the skin or open wound.

One manufacturer of PHMB is Avecia, Inc., located in Wilmington, Del., which sells a product known as COSMOCIL CQ™ which is an antimicrobial finish supplied at a concentrate of 20% PHMB in water. This finish is described as being particularly applicable to cotton blends and for cosmetic use such as medical devices and over the counter applications. However, it should be understood that other manufacturers of PHMB, as well as various formulas, may be used in accordance with the present invention.

There are various ways in which to apply the PHMB finish to a cellulosic wound dressing. For instance, PHMB may be applied to a cellulosic wound dressing by spraying or by adding PHMB to a water bath and feeding the gauze through prior to drying. However, it is important that the PHMB be applied evenly throughout the entire wound dressing, which is difficult to accomplish by spraying the PHMB onto the wound dressing. In addition, it is ideal to incorporate the treatment of the wound dressing with PHMB as part of the regular manufacturing process of cellulosic bandages from unfinished greige cloth. Preferably, PHMB is added to the wound dressing as part of the bleaching process.

With reference to FIG. 1, a typical bleaching process includes the use of a bleaching kier 10, in which a beam 12 of unfinished greige cloth is inserted. The kier 10 may be made out of stainless steel, as is well known in the art. The kier 10 is a pressurized vessel which allows fluids to be circulated within for treatment of the materials placed therein.

The greige cloth is rolled onto a perforated, hollow drum 14 into a beam of material 12. The construction of the hollow drum 14 is well known in the art, as disclosed in U.S. Pat. No. 3,596,481 to Wilcox, which is hereby incorporated by reference herein. In addition, a typical beam of cloth weighs approximately 950 lbs before bleaching, is approximately 4 feet wide, having a radius of approximately 3 feet, and is approximately 40,000 linear yards in length. Preferably, two beams of cloth are stacked within the vessel, weighing approximately 1900 lbs before bleaching. However, it should be understood that, dependent upon kier size, any number of beams of cloth may be prepared, depending on preference.

The rolled beams of greige cloth 12 are inserted into the kier 10, via an overhead crane, so that a fluid inlet line 20 is positioned and seated to the hollow drum 14, such that fluid may be directed into the internal surface of the hollow drum 14 and caused to flow radially outwardly through the rolled beams of greige cloth 12, in a manner well known in the art. While the present invention describes the use of only one perforated drum 14 per kier 10, it should be understood that a kier bleaching system uses multiple beams within a kier, as disclosed in U.S. Pat. No. 4,032,292 to Jones.

The fluid inlet line 20 is connected to a retention tank 22, which retains the bleaching solution to be released during the bleaching cycle. A heat exchanger 24 is connected between the retention tank 22 and the fluid inlet line 20, to heat the bleaching solution before it enters the kier 10. Heating the bleaching solution increases the rate at which the cloth is bleached.

In order to add the bleaching solution to the kier 10, valves 25 and 26 are opened, which causes water from a fresh water source 27 to flush out the bleaching fluid from the retention tank 22 towards a main valve 28. The main valve 28 is then opened to allow the bleaching fluid to flow to the eductor 30. Once the eductor valve 32 is opened, fresh water flushes the bleaching fluid from the retention tank 22 into the circulation cycle 33.

Pump 34 causes the bleaching fluid to be pumped through heat exchanger 24 and fluid inlet line 20 into the pressurized kier 10. The pump 34 also functions to recirculate the bleaching solution during the bleaching cycle. The wastewater of the system is released through the fluid outlet line 40 and pumped into the plant waste system via pump 44. This bleaching process is standard in the industry and is well known in the art.

Once the bleaching operation is complete, the resulting cloth decreases in weight from approximately 1900 lbs to approximately 1690 lbs. PHMB may now be added to the kier 10 by opening valve 50 and valve 25, which causes water from the fresh water source 27 to flush out the PHMB from the retention tank 52. The main valve 28 is then opened to allow the PHMB to flow to the eductor 30. Once the eductor valve 32 is opened, fresh water flushes the PHMB from the retention tank 52 into the circulation cycle 33. The pump 34 causes the PHMB to be pumped through the heat exchanger 24 and fluid inlet line 20, and into the pressurized kier 10.

All chemical additions and valving may be controlled by way of a computer, which is connected to the system. The computer control unit controls the kier processing parameters, and may include a diagram on the screen indicating the current cycle.

Although a number of chemicals may be used in the bleaching cycle, hydrogen peroxide is the active chemical responsible for bleaching the cloth. Hydrogen peroxide has the tendency to neutralize the PHMB. Therefore, before the PHMB is added, a chemical rinse and a wash water cycle should be conducted.

The kier 10 should then be filled with ambient clean water from fresh water source 54. Once the kier 10 is filled with water, the PHMB is then released from the retention tank 52 by opening eductor valve 32, and valves 25, 50, and 28 which causes fresh water to flush out the PHMB from the retention tank 52. The PHMB is circulated throughout the kier 10 by recirculation pump 34.

Alternatively, the PHMB may be pumped directly from the barrel in which it is sold into the kier 10, or any other way known in the art. Preferably, the PHMB is added to the kier 10 so that the volume of the PHMB introduced is measured to yield a concentration of between 0.10% and 0.80%, and preferably having 0.67% concentration within the kier 10.

The PHMB should be completely mixed, which should occur within 5 minutes, and the PHMB is circulated for preferably between 15–45 minutes, and more preferably about 30 minutes. In addition, the contact time may be longer, depending on kier size, fabric size, and pump strength. However, it should be understood that as the mixing time is expanded beyond 45 minutes, the amount of PHMB on the dressing may have an adverse effect on human tissue. The temperature of PHMB circulated throughout the kier 10 should be between 40° F. and 140° F., and preferably approximately 80° F. The kier pressure during the PHMB cycle should be between 5 psig and 40 psig, and preferably approximately 20 psig. Once the chemical circulation is complete, the kier wastewater is then drained into the plant waste system via pump 44.

The wet beam of cloth 12 is removed from the kier 10, now bleached and antimicrobially treated. The treated cloth is taken to a range station that concurrently processes multiple beams. The range station unwinds, folds, crimps, and dries the cloth and feeds the cloth into totes. Totes containing continuous amounts of cloth are then forwarded to cutting, folding, and packaging machines for each final product configuration.

The cellulosic bandages are preferably at least 50% cellulosic, and most preferably 100% cellulosic. The greater percentage of cellulose, the more effective the chemical bonding between the dressing and the PHMB. The final product configurations may include sponges, roll bandages, island dressings, and other wound dressings known in the art, such as a wound adhesive strip and the like. A gauze roll bandage typical includes 6-plies, and is approximately 4.5 inches by 4.1 yards. A gauze sponge may be approximately 6 inches by 6.75 inches along diagonals. The manufactured cellulosic wound dressings consist primarily of PHMB in an antimicrobial amount, without requiring an additional component such as an antibonding agent or an intermediate layer to prevent the normal reaction of PHMB to humans. However, it should be understood that other additives may be added to the cellulosic bandage, depending on preference.

The kier system used in accordance with the present invention may be manufactured by the company Gaston County Dyeing Machine Company, located in Stanley, N.C.

The use of PHMB on cellulosic bandages to cover open wounds has the benefit of retarding growth of bacteria in the dressing, but also retarding the migration of bacteria through the dressing. While PHMB is a broad spectrum agent, it is particulary effective against those organisms that contaminate acute and chronic wounds. PHMB is particularly effective against many types of bacteria including *Staphlylococcus aureus* and *Pseudomonas aeruginosa*. In addition, the PHMB can be used alone and without another component, to effectively kill bacteria, without causing irritation to a patient's skin, and more importantly, without causing irritation and preventing infection of the patient's open wound.

The following Example illustrates how the amount of chemical contained in the cloth was calculated. It is understood that the present invention is defined by the appended claims and not the specific details of this Example.

EXAMPLE

A beam of greige cloth was placed into a kier, and subsequently bleached. Once the bleaching was complete, PHMB was added to the kier to treat the beam of cloth. The PHMB used to treat the greige cloth was purchased from Avecia, Inc., which is sold as 20% active. The volume of the chemical introduced was measured to be 0.67% concentration within the kier (5 gallons PHMB/743 gallons water). The chemical was circulated for 30 minutes.

Extraction was conducted to establish the quantity of chemical attached to the cloth (grams PHMB/gram cloth). Extraction was conducted by soaking the cloth in 4% saline or 1M acetic acid overnight at a temperature of 56° C. PHMB in the resulting solution was identified via UV spectrophotometry or HPLC. This value is quantified by plotting the resulting peak against the standard dilution curve. The resulting loading level of PHMB was calculated to be between 1500–2500 ppm.

Although the present invention has been described with reference to certain preferred embodiments, it is apparent that modifications and variations thereof may be made by those skilled in the art without departing form the scope of the invention as defined by the following claims.

What is claimed is:

1. A method of covering an open wound, comprising the step of contacting a wound with a cellulosic bandage consisting essentially of an antimicrobial amount of PHMB applied to the bandage.

2. The method of claim 1, further comprising the step of directly contacting the open wound with the cellulosic bandage without requiring an intermediate layer.

3. The method of claim 1, wherein the antimicrobial amount of PHMB applied to the bandage is between 1500–2500 ppm.

4. The method of claim 1, wherein the cellulosic bandage is between 50% to 100% cellulosic.

5. The method of claim 1, wherein the cellulosic bandage is an island dressing.

6. The method of claim 1, wherein the cellulosic bandage is a sponge.

7. The method of claim 1, wherein the cellulosic bandage is a roll bandage.

8. A method of manufacturing a wound dressing having antimicrobial properties, comprising the steps of:

A) providing at least one rolled beam of cellulosic material;
   B) inserting the beam of material into an enclosed vessel;
   C) adding PHMB into the vessel, wherein the volume of PHMB added to the vessel is between 0.10% and 0.80% of the total water volume; and
   D) circulating the PHMB for a predetermined period of time.

9. The method of claim 8, wherein the at least one beam of material is rolled onto a perforated drum and the PHMB is added into the vessel through the perforated drum.

10. The method of claim 9, further comprising the step of bleaching the beam of material before said step of adding PHMB into the vessel.

11. The method of claim 10, wherein said bleaching step is performed by pumping bleaching agents into the vessel through the perforated drum.

12. The method of claim 10, further comprising the step of chemically rinsing the beam of material after said bleaching step and before said step of adding PHMB into the vessel.

13. The method of claim 12, further comprising the step of filling the enclosed vessel with water after said rinsing step and prior to said step of adding PHMB into the vessel.

14. The method of claim 8, wherein said circulating step is performed for approximately between 15 and 45 minutes.

15. The method of claim 14, wherein said circulating step is performed for approximately 30 minutes.

16. The method of claim 15, wherein the volume of PHMB added to the vessel during said step of adding PHMB is approximately 0.67% of the total water volume.

17. The method of claim 8, further comprising the step of draining the wastewater into a plant waste water system.

18. The method of claim 8, further comprising the steps of:

A) removing the beams of material from the enclosed vessel; and
   B) unwinding the material for further processing.

19. The method of claim 8, wherein said step of circulating the PHMB is caused by directing the PHMB through the perforated drum and in a direction radially outwardly.

20. A product manufactured according to the method of claim 8.

21. A cellulosic wound dressing consisting essentially of an antimicrobial amount of PHMB.

22. The wound dressing of claim 21, wherein the antimicrobial amount of PHMB applied to the bandage is between 1500–2500 ppm.

23. The wound dressing of claim 21, wherein the cellulosic bandage is between 50% to 100% cellulosic.

24. The wound dressing of claim 21, wherein the cellulosic bandage is an island dressing.

25. The wound dressing of claim 21, wherein the cellulosic bandage is a sponge.

26. The wound dressing of claim 21, wherein the cellulosic bandage is a roll bandage.

* * * * *